(12) United States Patent
Key et al.

(10) Patent No.: US 7,544,272 B2
(45) Date of Patent: Jun. 9, 2009

(54) APPARATUS FOR $C_2$ RECOVERY

(75) Inventors: Ronald D. Key, Tulsa, OK (US); William G. Brown, Tulsa, OK (US)

(73) Assignee: Linde Process Plants, Inc., Tulsa, OK (US)

( * ) Notice: Subject to any disclaimer, the term of this patent is extended or adjusted under 35 U.S.C. 154(b) by 1526 days.

(21) Appl. No.: 09/931,218

(22) Filed: Aug. 16, 2001

(65) Prior Publication Data
US 2002/0042551 A1 Apr. 11, 2002

Related U.S. Application Data

(62) Division of application No. 09/527,175, filed on Mar. 17, 2000, now Pat. No. 6,278,035.

(51) Int. Cl.
*B01D 3/00* (2006.01)
(52) U.S. Cl. ......................... 202/82; 202/154
(58) Field of Classification Search .............. 202/82, 202/154
See application file for complete search history.

(56) References Cited

U.S. PATENT DOCUMENTS

| | | | | |
|---|---|---|---|---|
| 4,869,740 A * | 9/1989 | Campbell et al. | ............ | 62/621 |
| 4,895,584 A * | 1/1990 | Buck et al. | ............ | 62/621 |
| 5,771,712 A * | 6/1998 | Campbell et al. | ............ | 62/621 |
| 5,799,507 A * | 9/1998 | Wilkinson et al. | ............ | 62/621 |
| 6,182,469 B1 * | 2/2001 | Campbell et al. | ............ | 62/621 |
| 6,278,035 B1 * | 8/2001 | Key et al. | ............ | 585/800 |
| 6,311,516 B1 * | 11/2001 | Key et al. | ............ | 62/619 |
| 6,712,880 B2 * | 3/2004 | Foglietta et al. | ............ | 95/184 |

* cited by examiner

*Primary Examiner*—Tam M Nguyen
(74) *Attorney, Agent, or Firm*—Millen, White, Zelano, Branigan, P.C.

(57) ABSTRACT

An improved process for separating a hydrocarbon bearing feed gas containing methane and lighter, $C_2$ (ethylene and/or ethane), and heavier components into a fraction containing predominantly methane and lighter components and a fraction containing predominantly $C_2$ and heavier hydrocarbon components including the steps of cooling and partially condensing and delivering the feed stream to a separator to provide a first residue vapor and a first liquid containing $C_2$, directing a first part of the first liquid containing $C_2$ into a heavy-ends fractionation column wherein the liquid is separated into a second hydrocarbon bearing vapor residue and a second liquid product containing $C_2$; further cooling the second part of the first liquid containing $C_2$ and partially condensing the second hydrocarbon bearing vapor residue; combining the cooled second part of the first liquid and partially condensed second hydrocarbon-bearing vapor residue and directing them to a second separator effecting a third residue and a third liquid; cooling and directing a first part of the third liquid into the lights-ends fractionation column, to thereby condense $C_2$'s and heavier components while the methane is evaporated in the light-ends fractionation column to thereby obtain fourth residue vapor and liquid, heating and supplying the fourth liquid recovered from the light-ends fractionation column to the heavy-ends fractionation column as a feed thereto; conducting the second part of the third liquid to the heavy-ends fractionation column as a feed thereto.

20 Claims, 2 Drawing Sheets

APPARATUS FOR C₂ RECOVERY

This is a divisional application of application Ser. No. 09/527,175, Filed Mar. 17, 2000 now U.S. Pat. No. 6,278,035.

BACKGROUND OF THE INVENTION

1. Field of the Invention

This invention relates to an improved process for separating a hydrocarbon-bearing feed gas which contains methane and lighter components, (not necessarily all hydrocarbon components), $C_2$ (ethylene and ethane), and heavier hydrocarbon components into two fractions. The first fraction contains predominantly methane and lighter components and the second fraction contains the recovered desirable $C_2$ and heavier components. More particularly, this invention relates to a process and apparatus wherein the yield of $C_2$'s is increased or alternatively energy consumption is reduced for a given $C_2$ recovery.

2. The Prior Art

Hydrocarbon-bearing gas may contain lighter components (e.g., hydrogen, nitrogen, etc.) methane, ethane, and/or ethylene, and a substantial quantity of hydrocarbons of higher molecular weight, for example, propane, butane, pentane and often their unsaturated analogs. Recent changes in ethylene/ethane demand have created increased markets for ethylene/ethane and have created a need for more efficient processes which yield higher recovery levels of this product. In more recent times, the use of cryogenic processes utilizing the principle of gas expansion through a mechanical device to produce power while simultaneously extracting heat from the system have been employed. The use of such equipment depends upon the pressure of the gas source, the composition of the gas and the desired end results. In the typical cryogenic expansion-type recovery processes used in the prior art, a gas stream under pressure is cooled by heat exchange with other streams of the process and/or external sources of cooling are employed such as refrigeration systems. As the gas is cooled, liquids are condensed and are collected and separated so as to thereby obtain desired hydrocarbons. The high pressure liquid feed is typically transferred to a demethanizer column after the pressure is adjusted to the operating pressure of the demethanizer. In column after the pressure is adjusted to the operating pressure of the demethanizer. In such fractionating column the liquid feed is fractionated to separate the residual methane and lighter components from the desired products of ethylene/ethane and heavier hydrocarbon components. In the ideal operation of such separation processes, the vapors leaving the process contain substantially all of the methane and lighter components found in the feed gas and substantially no ethylene/ethane or heavier hydrocarbon components remain. The bottom fraction leaving the demethanizer typically contains substantially all of the ethylene/ethane and heavier hydrocarbon components with very little methane or lighter components which is discharged in the fluid gas outlet from the demethanizer.

A patentability search was conducted on the present invention and the following references were uncovered.

| Inventor | Pat. No. | Issue Date |
|---|---|---|
| Harandi | 4,664,784 | May 12, 1987 |
| Buck et al | 4,895,584 | Jan. 23, 1990 |
| Campbell et al | 5,771,712 | Sep. 1, 1998 |
| Wilkinson et al | 5,699,507 | Jun. 30, 1998 |

U.S. Pat. No. 4,664,784—Issued May 12, 1987
M. N. Harandi to Mobil Oil Corporation In a reference directed to fractionation of hydrocarbon mixtures, teachings are found on column 4, line 32 et sequitur re: a zone (81) wherein a descending liquid heavy-ends portion contacts an ascending vaporous light-ends portion so as ". . . to aid in heat transfer between vapor and liquid." (column 4, line 44).

U.S. Pat. No. 4,895,584—Issued Jan. 23, 1990
L. L. Buck et al to Pro-Quip Corporation A reference that claims an improved process for hydrocarbon separation and teaches supplying of the liquids recovered from the light-ends fractionating column to the heavy ends fractionating column and directing part of the ($C_2$ containing) liquid from a first step into intimate contact with a second residue, which liquid provides additional liquefied methane which acts with the partially condensed second residue as a direct contact refrigerant to thereby condense $C_2$ and heavier comprising hydrocarbons while methane itself is evaporated in the light-ends fractionation column.

On column 1, lines 56-67 the following teachings are found: ". . . feed gas is first cooled and partially condensed and delivered to a separator to provide a first residue vapor and a liquid containing $C_2$. . . Part of the liquid containing $C_2$ from the separator may be directed into a heavy-ends fractionation column wherein the liquid is separated into a second residue containing lighter hydrocarbons and $C_2$ containing products. A part of the first residue vapors with at least part of the partially condensed second residue are counter currently contacted and commingled in a light-ends fractionation column (emphasis added) . . . "

On column 2, lines 1-10 the following teachings are found: "The liquids recovered from the light-ends fractionation column are then fed to the heavy-ends fractionation column as a liquid feed. A portion of the liquids containing $C_2$ from the separator is fed into intimate contact with the second residue prior to discharging the commingled liquids and gases into the light-ends fractionation column to thereby achieve mass and heat transfer (emphasis added) to thereby liquefy a higher percent of the $C_2$ and heavier hydrocarbon components while the methane is vaporized" (column 2, lines 1-10).

The following Elcor Corporation references describe the recovery of $C_3$ and heavier hydrocarbons via processes wherein counter-current contact of a stream drawn from a deethanizer with a stream in a separator/absorber takes place:

U.S. Pat. No. 5,799,507- Issued Sep. 1, 1998
J. D. Wilkinson et al to Elcor Corporation See column 4, line 2 re: ". . . liquid portion of expanded stream commingles with liquids falling downward from the absorbing section . . . " I.o.w., the stream (36) from the deethanizer (17) flows through heat exchanger (20) to become Stream (36a) which flows into the upper section of separator (15) where it ". . . contacts the vapors rising upward through the absorption section" (column 5, lines 3-4).

U.S. Pat. No. 5,771,712- Issued Jun. 30, 1998
R. E. Campbell et al to Elcor Corporation This reference teaches essentially the same as Wilkinson et al.

None of the foregoing patents discussed above embody the present invention.

SUMMARY OF THE INVENTION

The present invention provides processes for increasing the ethylene and ethane component of the discharge from the process unit at reduced energy consumption than the prior art. The foregoing advantage is achieved in the present invention by a process in which the feed gas is first cooled and partially condensed and delivered to a separator to provide a first residue vapor and a first liquid containing $C_2$ which liquid also contains lighter hydrocarbons. A first part of the first liquid containing $C_2$ from the separator may be directed into a heavy-ends fractionation column, wherein the liquid is separated into a second residue containing lighter hydrocarbons and a second liquid product containing $C_2$. A second part of the first liquid from the separator is cooled. The second residue is cooled and partially condensed and then combined with the cooled second part of the first liquid providing, upon separation, a third residue and a third liquid. A first part of the third liquid is cooled and fed to the light-ends fractionation column. A second part of the third liquid is fed directly to the heavy-ends fractionation column. A part of the first residue vapor with a cooled first part of the third liquid are countercurrently contacted and commingled in a light-ends fractionation column to thereby provide fourth residue vapor and liquid which are separately discharged. Cooling the first part of the third liquid prior to its introduction into the light-ends fractionation column aids in mass and heat transfer. This cooling thereby provides for greater liquefaction of a higher percent of the $C_2$ and heavier hydrocarbon components while the methane contained in the first part of the third liquid is vaporized. The fourth liquid recovered from the light-ends fractionation column is heated then introduced to the heavy-ends fractionation column as a feed.

A better understanding of the invention will be had with reference to the following description and claims, taken in conjunction with the attached drawings.

DESCRIPTION OF THE PREFERRED EMBODIMENTS

The improved processes of the present disclosure include the steps of cooling a gaseous hydrocarbon-containing feed stream to form a first vapor stream and a first liquid stream. A first part of the first liquid stream is transferred to a heavy-ends fractionation column while the first vapor stream is transferred to the bottom of a light-ends fractionation column. The heavy-ends fractionation column overhead vapor, which consists mainly of methane, ethylene, and/or ethane, is cooled and partially condensed. The cooled heavy-ends fractionation column overhead is combined with a cooled second part of the first liquid stream. The resulting stream is fed to a separator and separated into a third residue vapor and a third liquid. A first part of the third liquid is cooled and fed to the upper portion of the light-ends fractionation column. The liquid flows downwardly within the light-ends fractionation column and contacts gaseous ethylene and/or ethane and heavier hydrocarbons that flow upwardly. The methane portion of the liquid stream is vaporized by absorbing heat from the gaseous ethylene/ethane and heavier hydrocarbons which causes the ethylene/ethane and heavier hydrocarbons to condense and exit at the bottom of the light-ends fractionation column. The gaseous methane and lighter components within the light-ends fractionation column are removed from the overhead as a product of the process. The second part of the third liquid may be used to reflux the heavy-ends fractionation column. The fourth liquid at the bottom of the light-ends fractionation column is removed and used to cool other process streams; the thus-heated fourth liquid is fed to the upper portion of the heavy-ends fractionation column. The liquid at the bottom of the heavy-ends fractionation column is removed as a product of the process.

Figure 1:
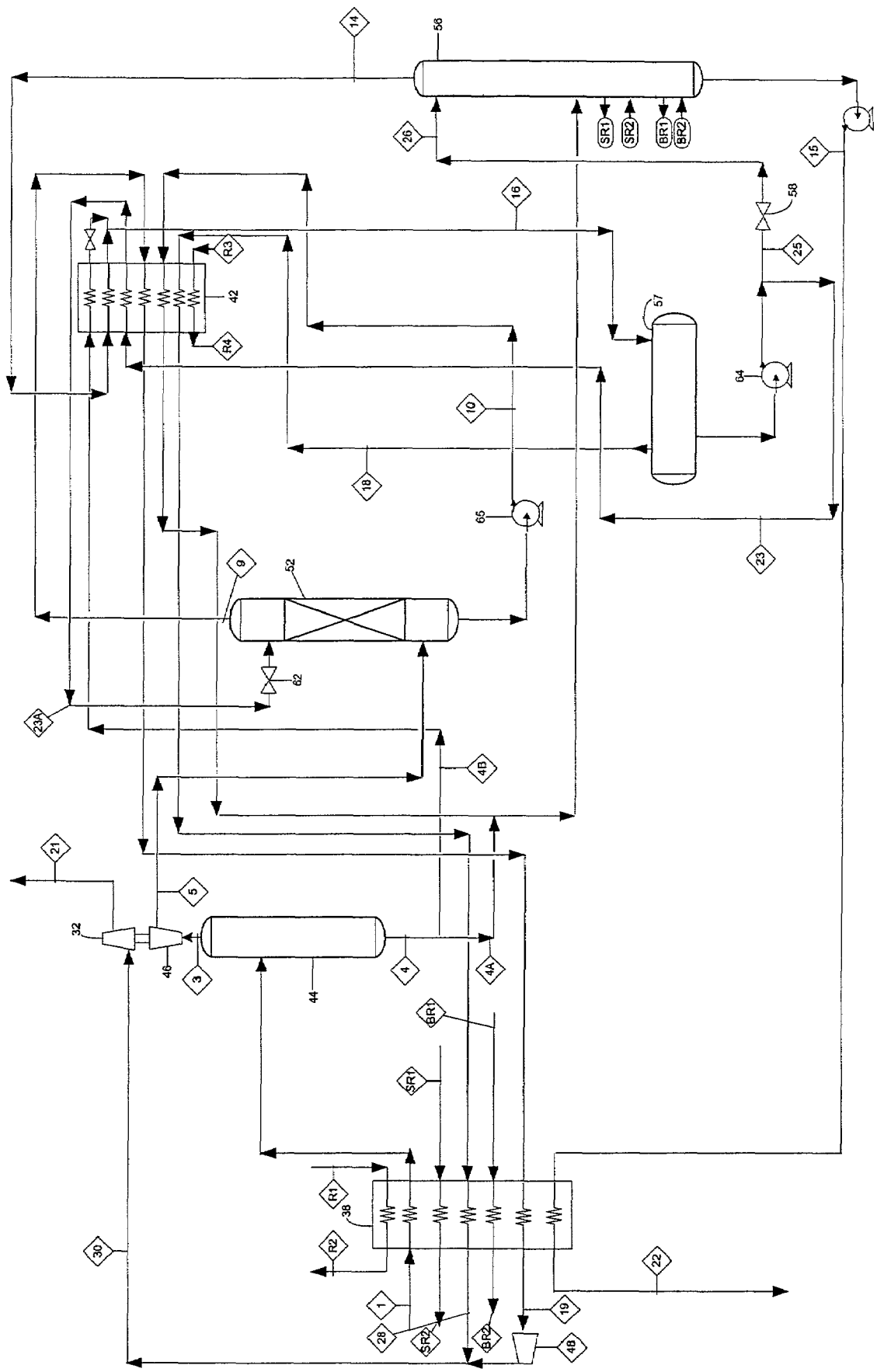
FIG. 1 is a schematic flow diagram illustrating a method of practicing a preferred embodiment of the invention.

The improved process of this invention is illustrated in a first embodiment in FIG. 1. The incoming gas stream 1 at a temperature of 120° F. and a pressure of 827 psia passes through heat exchanger 38, so that the temperature thereof is reduced to about −72° F. with attendant partial condensation. Pressure is reduced as the gas flows through the heat exchangers resulting in a pressure of 812 psia at −72° F. at which the raw gas is delivered into a separator 44. Within separator 44 the cooled gas stream is separated into a first liquid stream (stream 4) and a first residue vapor, stream 3. Stream 3 is passed through a turbo expander 46. The shaft of turbo expander 46 is connected directly to the shaft of the booster compressor 32. From the turbo expander, the first residue gas having a temperature of about −163° F. at 200 psia passes by way of stream 5 into a light-ends fractionation column 52.

From separator 44 a first part of the first liquid containing $C_2$ is conducted into a heavy-ends fractionation column 56 by way of stream 4A. A second part of the first liquid containing $C_2$ from stream 4 is channeled by way of stream 4B through heat exchanger 42 where its temperature is decreased. The cooled liquid exits the heat exchanger and combines with the cooled residue stream 14 to form stream 16.

The second residue from heavy-ends fractionation column 56, having a temperature of about −132° F., is fed by way of stream 14 through heat exchanger 42, combines with the remainder of the liquid containing $C_2$ from stream 4B above, and by way of stream 16 into the reflux separator 57. A first part of the third liquid from the reflux separator 57 is routed by stream 23 through heat exchanger 42 where its temperature is reduced. This liquid stream is then passed as stream 23A into the light-ends fractionation column 52. The liquid from stream 23A passes downwardly through the light-ends fractionation column 52 and encounters the rising first residue gas from stream 5 so that mass and latent heat transfer occur. The second part of the third liquid from the reflux separator 57 is routed by stream 26 to the heavy-ends fractionation column 56.

The light-ends fractionation column 52 functions as a combination heat and mass transfer device. The column has two feed streams; that is, streams 5 and 23A, and two product streams; that is, streams 10 and 9. The light-ends fractionation column 52 consists of at least one, and preferably more, theoretical liquid-vapor equilibrium stages.

Vapor enters the light-ends fractionation column by way of stream 5 as a bottom feed while the top feed is by way of stream 23A which is a liquid enriched by condensed methane. The methane and lighter constituents and un-recovered ethylene and ethane, exit as a dew point vapor as a fourth residue (stream 9) from the top tray or separation stage of the light-ends fractionation column 52.

The top feed through stream 23A into the light-ends fractionation column 52 and particularly the methane content thereof serves as a reflux in the column. In flowing from stage to stage within column 52, the liquid methane is vaporized and in turn the liquid is progressively enriched in ethylene and ethane condensed from the upflowing bottom feed vapor from stream 5.

The fourth liquid stream from the light-ends fractionation column 52, stream 10, provides process cooling in exchanger 42 while it is itself warmed and then fed to the heavy-ends fractionation column 56 for further separation.

The fourth residue gas (stream 9) discharged from light-ends fractionation column 52 passes through exchangers 42 and 38 and exits the heat exchanger system as stream 19. The third residue gas vapor in stream 18 exiting the reflux separator 57 also pass through exchangers 42 and 38 and exit the heat exchanger system as stream 28. The warmed vapor from the light-ends fractionation column (stream 19) is compressed in compressor 48 to the same pressure as stream 28 and combined with stream 28 to form stream 30. The combined vapors of stream 30 are compressed in the booster compressor 32. At this stage, the methane rich off-gas in stream 21 has a temperature of 103° F. and a pressure of 187 psia. If it is desired to return the discharge gas to the same system from which the raw gas was taken, such as for further transportation of the gas, the pressure will need to be raised back to that substantially equal to the incoming pressure of 827 psia in stream 1.

The second liquid discharge, rich in $C_2$ content, from the lower end of the heavy-ends fractionation column 56 is passed by way of stream 15 and exchanger 38 to product discharge stream 22.

The result of a simulation of the process of FIG. 1 is set forth in Table 1A wherein the moles per hour of various constituents of the streams are set forth. The process achieves a recovery of about 97.37 percent of the $C_2$ content of the feed gas in addition to substantially complete recovery of the $C_3$ and heavier hydrocarbon components of the feed gas stream into the less volatile fraction (product).

Table 1B relates the moles per hour of various constituents of the stream of the process of FIG. 1 when the process of FIG. 1 is applied to a feed gas stream that is enriched in ethane and heavier components.

Figure 2:
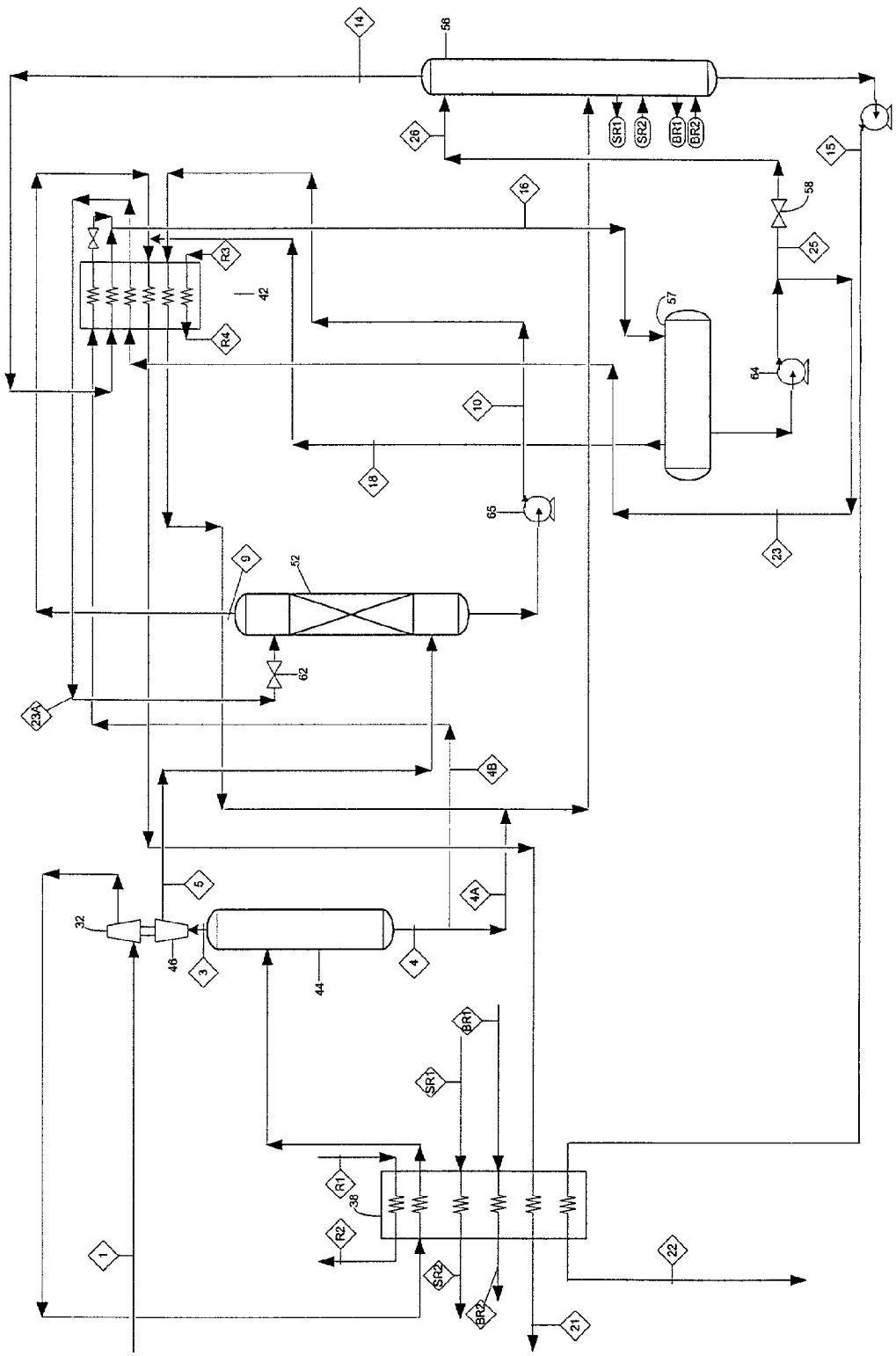
FIG. 2 is a schematic flow diagram illustrating a variation in the preferred embodiment of the present invention.

FIG. 2 shows an alternate embodiment of the invention. The components of the process of FIG. 2 having the same basic structure and function of those of the system of FIG. 1 are given like numbers. The process is as described with reference to FIG. 1, except that the booster compressor 32 is placed on the feed gas (stream 1) and streams 9 and 18 are combined prior to exchanger 42.

Table 2, shows the result of a simulation of the system of FIG. 2. Table 2 provides the moles per hour of various constituents for the various streams of this embodiment of the process. The process achieves a recovery of about 91.64 percent of the ethylene and 96.77 percent of the ethane content of the feed gas in addition to substantially complete recovery of the $C_3$ and heavier hydrocarbon components of the feed gas stream in to the less volatile fraction (product).

The process has been illustrated using various standard components employed for the sequence of treating steps with it being understood that the process may be practiced utilizing different physical apparatus. For instance, the turbo expander can, in many instances, be eliminated or replaced by a Joule-Thomson isenthalpic control valve. The difference is that where the expander is eliminated or where the Joule-Thomson valve is substituted for the turbo expander, normally greater inlet and refrigeration compression duties are required.

A different arrangement has been shown in the alternate embodiment for cooling the second residue effluent and thus providing reflux to the light-ends fractionation and heavy-ends fractionation columns.

Some of the processes in each instance may use multiple turbo expanders. The desirability of the use of multiple turbo expanders is predicated primarily upon the amount of hydrogen content of the inlet gas in stream 1. It is understood that, according to the inlet gas content, only single turbo expanders may be employed in practicing the process; or, in some instances as previously indicated, turbo expanders may be eliminated completely or substituted by one or more Joule-Thomson isenthalpic expansion valves.

An important feature of the process is the employment of the light-ends fractionation column 52 which functions as a combination heat and mass transfer device. The use of the reflux in the top stage means that the liquid methane of the reflux is vaporized; and in turn the liquid is progressively enriched in ethylene and ethane condensed from the upflowing bottom feed vapor to thereby recover a higher percent of the $C_2$ components.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

TABLE 1A

THE PRO-QUIP CORPORATION

| STREAM NAME | STREAM NUMBER | | | | | | | | | |
|---|---|---|---|---|---|---|---|---|---|---|
| | 1 | 3 | 4 | 5 | 9 | 10 | 14 | 16 | 18 | 23 |
| NITROGEN | 99 17 | 93 86 | 5 31 | 93 86 | 92 74 | 2 50 | 7 81 | 7 81 | 6.43 | 1.38 |
| CARBON DIOXIDE | 8.64 | 6 19 | 2 45 | 6 19 | 1 89 | 5 83 | 1 95 | 1 95 | 0.42 | 1.53 |
| METHANE | 7552.91 | 6526.79 | 1026 12 | 6526 79 | 6374 89 | 1115 68 | 2131 34 | 2131 34 | 1168 58 | 963 78 |
| ETHANE | 486 41 | 272 65 | 213 76 | 272 65 | 9 22 | 299 03 | 39 18 | 39 18 | 3 57 | 35 60 |
| PROPANE | 198 31 | 56.60 | 141 71 | 56 60 | 0 04 | 58 45 | 1 92 | 1 92 | 0 03 | 1 89 |
| I-BUTANE | 36.66 | 5 59 | 31.07 | 5.59 | 0 00 | 5.67 | 0 08 | 0 08 | 0 00 | 0.08 |
| N-BUTANE | 63 30 | 7.19 | 56 11 | 7 19 | 0 00 | 7 27 | 0 08 | 0 08 | 0 00 | 0.08 |
| I-PENTANE | 20 83 | 1.16 | 19 67 | 1 16 | 0.00 | 1 17 | 0 01 | 0 01 | 0 00 | 0.01 |
| N-PENTANE | 20.63 | 0.86 | 19 77 | 0 86 | 0.00 | 0 86 | 0 00 | 0 00 | 0 00 | 0 00 |
| HEXANE | 19.29 | 0 29 | 19 00 | 0 29 | 0 00 | 0 29 | 0 00 | 0 00 | 0 00 | 0 00 |
| TOTAL LBMOL/HR | 8525 10 | 6971 27 | 1553 83 | 6971 27 | 6478 78 | 1496.83 | 2,182 36 | 2,182 36 | 1179.02 | 1004.35 |
| MASS FLOW LB/HR | 160249 | 119227 | 41022 | 119227 | 105232 | 30726 | 35770 | 35770 | 19055 | 16732 |
| VOLUME FLOW MMSCFD | 78 | 63 | — | — | 59 | — | 20 | — | 11 | — |
| MOL MOLE, WT | 18 80 | 17 10 | 26 40 | 17 10 | 16 24 | 20 53 | 16 39 | 16 39 | 16 16 | 16.66 |

TABLE 1A-continued

THE PRO-QUIP CORPORATION

| | | | | | | | | | | |
|---|---|---|---|---|---|---|---|---|---|---|
| DENSITY LB/FT³ | 2 83 | 5 92 | 26 30 | 1.51 | 1.32 | 26 94 | 2 06 | 4 01 | 2 35 | 20 51 |
| TEMPERATURE ° F. | 120 | −72 | −72 | −163 | −178 | −165 | −132 | −153 | −153 | −153 |
| PRESSURE PSIA | 827.00 | 812 00 | 812 00 | 200 00 | 193 00 | 385 00 | 330 00 | 328 00 | 328 00 | 353 00 |

| STREAM NAME | STREAM NUMBER | | | | | Percent Recovered to Volatile Fraction | Percent Recovered To Less Volatile Fraction |
|---|---|---|---|---|---|---|---|
| | 25 | 26 | 15 | 22 | 21 | | |
| NITROGEN | 0 00 | 0 00 | 0 00 | 0 00 | 99 17 | 100 00% | 0 00% |
| CARBON DIOXIDE | 0 00 | 0 00 | 6 33 | 6 33 | 2 31 | 26 71% | 73 30% |
| METHANE | 0 00 | 0.00 | 10 46 | 10 46 | 7543 46 | 99 87% | 0 14% |
| ETHANE | 0.00 | 0 00 | 473 61 | 473.61 | 12 79 | 2 63% | 97 37% |
| PROPANE | 0.00 | 0 00 | 198 24 | 198 24 | 0 07 | 0 04% | 99 96% |
| I-BUTANE | 0.00 | 0 00 | 36 66 | 36.66 | 0 00 | 0 00% | 100 00% |
| N-BUTANE | 0 00 | 0 00 | 63 30 | 63 30 | 0 00 | 0 00% | 100 00% |
| I-PENTANE | 0 00 | 0 00 | 20 83 | 20 83 | 0.00 | 0 00% | 100 00% |
| N-PENTANE | 0 00 | 0 00 | 20 63 | 20 63 | 0 00 | 0 00% | 100 00% |
| HEXANE | 0 00 | 0 00 | 19 29 | 19 29 | 0 00 | 0 00% | 100 00% |
| TOTAL LBMOL/HR | 0 00 | 0 00 | 868.31 | 868 31 | 7657 80 | | |
| MASS FLOW LB/HR | 0 | 0 | 35978 | 35978 | 124286 | | |
| VOLUME FLOW MMSCFD | — | — | — | — | 70 | | |
| MOLE WT | 16 66 | 16 66 | 41.44 | 41 44 | 16.23 | | |
| DENSITY LB/FT³ | 20.51 | 20 51 | 30 11 | 27.97 | 1.03 | | |
| TEMPERATURE ° F. | −153 | −153 | 71 | 100 | 167 | | |
| PRESSURE PSIA | 353 00 | 353 00 | 500 00 | 495 00 | 413 41 | | |

TABLE 1B

THE PRO-QUIP CORPORATION

| STREAM NAME | STREAM NUMBER | | | | | | | | | |
|---|---|---|---|---|---|---|---|---|---|---|
| | 1 | 3 | 4 | 5 | 9 | 10 | 14 | 16 | 18 | 23 |
| NITROGEN | 345 88 | 280 87 | 65 02 | 280 87 | 275 89 | 16.91 | 19.90 | 84.91 | 69.99 | 11.93 |
| CARBON DIOXIDE | 327 77 | 161 06 | 166 70 | 161.06 | 48 44 | 254.24 | 37.16 | 203 85 | 26 83 | 141.62 |
| METHANE | 24864 18 | 16379 96 | 8484 21 | 16379 96 | 17115 17 | 6530 39 | 8271 66 | 16754 42 | 7672.43 | 7265 60 |
| ETHANE | 3696 03 | 1309.26 | 2386 76 | 1309.26 | 179 47 | 3053 40 | 131 47 | 2518 25 | 113 74 | 1923.61 |
| PROPANE | 2012 72 | 363 60 | 1649 12 | 363 60 | 10 96 | 1673 25 | 11 09 | 1660 25 | 9 49 | 1320 61 |
| I-BUTANE | 385.41 | 40 55 | 344.87 | 40 55 | 0 43 | 316 09 | 0 54 | 345 41 | 0 46 | 275.96 |
| N-BUTANE | 612.71 | 50 73 | 561 98 | 50 73 | 0 35 | 500 03 | 0 49 | 562 47 | 0 41 | 449.65 |
| I-PENTANE | 151.53 | 7 05 | 144 48 | 7 05 | 0 02 | 122 62 | 0 03 | 144 51 | 0.03 | 115.59 |
| N-PENTANE | 115 29 | 4.29 | 111 00 | 4 29 | 0 01 | 93 09 | 0 01 | 111 02 | 0 01 | 88.80 |
| HEXANE | 98 82 | 1 67 | 97 15 | 1.67 | 0.00 | 79 39 | 0.00 | 97.15 | 0.00 | 77 72 |
| HYDROGEN SULFIDE | 0.00 | 0 00 | 0 00 | 0 00 | 0.00 | 0 00 | 0 00 | 0 00 | 0 00 | 0.00 |
| CARBONYL SULFIDE | 3 29 | 0 68 | 2 61 | 0 68 | 0 03 | 2 74 | 0 03 | 2 64 | 0 03 | 2 09 |
| TOTAL LBMOL/HR | 32613.64 | 18599.74 | 14013 90 | 18599 74 | 17630 77 | 12642 15 | 8472 40 | 22484 88 | 7893 41 | 11673 17 |
| MASS FLOW LB/HR | 708883 | 339451 | 369432 | 339451 | 290366 | 352036 | 139402 | 508812 | 130123 | 302951 |
| VOLUME FLOW MMSCFD | 297 | 169 | — | — | 161 | — | 77 | — | 72 | — |
| MOLE. WT, | 21 74 | 18.25 | 26.36 | 18 25 | 16.47 | 27.85 | 16 45 | 22 63 | 16.48 | 25.95 |
| DENSITY LB/FT³ | 4 20 | 6 88 | 24.02 | 1.76 | 1.46 | 32.32 | 2 07 | 6 70 | 2.06 | 30.02 |
| TEMP ° F. | 120 | −40 | −40 | −133 | −149 | −138 | −129 | −131 | −131 | −131 |
| PRESSURE PSIA | 978 00 | 966 35 | 966 35 | 242 00 | 237 00 | 375 00 | 335 00 | 330 00 | 330 00 | 370 00 |

| STREAM NAME | STREAM NUMBER | | | | | Percent Recovered to Volatile Fraction | Percent Recovered To Less Volatile Fraction |
|---|---|---|---|---|---|---|---|
| | 25 | 26 | 15 | 22 | 21 | | |
| NITROGEN | 2 98 | 2 98 | 0 00 | 0 00 | 345 88 | 100 00% | 0 00% |
| CARBON DIOXIDE | 35 40 | 35 40 | 252 48 | 252 48 | 75 27 | 22 97% | 77 03% |

TABLE 1B-continued

THE PRO-QUIP CORPORATION

|  |  |  |  |  |  |  |  |
|---|---|---|---|---|---|---|---|
| METHANE | 1816 40 | 1816 40 | 75 13 | 75 13 | 24787 60 | 99 69% | 0 30% |
| ETHANE | 480 90 | 480 90 | 3402 83 | 3402 83 | 293 21 | 7 93% | 92 07% |
| PROPANE | 330 15 | 330 15 | 1992 30 | 1992 30 | 20 46 | 1 02% | 98 99% |
| I-BUTANE | 68 99 | 68 99 | 384 53 | 384 53 | 0 89 | 0 23% | 99 77% |
| N-BUTANE | 112 41 | 112 41 | 611 95 | 611 95 | 0 76 | 0 12% | 99 88% |
| I-PENTANE | 28 90 | 28 90 | 151 49 | 151 49 | 0 04 | 0 03% | 99 97% |
| N-PENTANE | 22 20 | 22 20 | 115 28 | 115 28 | 0 02 | 0 02% | 99 98% |
| HEXANE | 19 43 | 19 43 | 98 82 | 98 82 | 0 00 | 0 00% | 00 00% |
| HYDROGEN SULFIDE | 0 00 | 0 00 | 0 00 | 0 00 | 0 00 | 0 00% | 00 00% |
| CARBONYL SULFIDE | 0 52 | 0 52 | 3 23 | 3 23 | 0 06 | 1 84% | 98 16% |
| TOTAL LBMOL/HR | 2918 29 | 2918 29 | 7088 04 | 7088 04 | 25524 18 | | |
| MASS FLOW LB/HR | 75738 | 75738 | 288372 | 288372 | 420489 | | |
| VOLUME FLOW MMSCFD | — | — | — | — | 232 | | |
| MOLE WT | 25 95 | 25 95 | 40 68 | 40 68 | 1647 | | |
| DENSITY LB/FT$^3$ | 30 02 | 30 02 | 30 09 | 27 83 | 0 88 | | |
| TEMPERATURE °F. | −131 | −131 | 72 | 100 | 115 | | |
| PRESSURE PSIA | 370 00 | 370 00 | 500 00 | 490 00 | 317 14 | | |

TABLE 2

THE PRO-QUIP CORPORATION

| STREAM NAME | STREAM NUMBER | | | | | | | | | |
|---|---|---|---|---|---|---|---|---|---|---|
|  | 1 | 3 | 4 | 5 | 9 | 10 | 14 | 16 | 18 | 23 |
| HYDROGEN | 1274.20 | 1203.16 | 71 03 | 1203 16 | 1200 28 | 3 85 | 29 12 | 75 29 | 73.92 | 0 96 |
| NITROGEN | 197 10 | 165 03 | 32 07 | 165 03 | 162 81 | 5 39 | 17 96 | 38 80 | 34.30 | 3.16 |
| CARBON MONOXIDE | 13 01 | 10.54 | 2 47 | 10.54 | 10 36 | 0 52 | 1 53 | 3 13 | 2 65 | 0 34 |
| METHANE | 3194 56 | 1790 74 | 1403 81 | 1790 74 | 1992 70 | 641 30 | 1485 42 | 2397 90 | 1197 69 | 843.29 |
| ETHYLENE | 672 81 | 127 55 | 545 26 | 127.55 | 29 42 | 356 01 | 39 41 | 393 82 | 26 82 | 257.87 |
| ETHANE | 1402 52 | 155 95 | 1246 57 | 155 95 | 21 51 | 711 58 | 34 92 | 845 19 | 23 80 | 577 13 |
| PROPENE | 195 47 | 5.89 | 189.58 | 5.89 | 0.24 | 92 39 | 0 64 | 123 86 | 0.41 | 86.74 |
| PROPANE | 156.55 | 3 57 | 152 98 | 3 57 | 0 12 | 73 40 | 0 35 | 99 79 | 0 22 | 69 96 |
| I-BUTANE | 1 51 | 0 01 | 1 50 | 0 01 | 0 00 | 0 70 | 0 00 | 0 98 | 0 00 | 0.68 |
| N-BUTANE | 81 73 | 0 45 | 81 28 | 0.45 | 0 00 | 37 57 | 0 02 | 52 86 | 0 01 | 37 13 |
| N-PENTANE | 28 36 | 0.03 | 28.33 | 0.03 | 0 00 | 12.97 | 0.00 | 18 42 | 0 00 | 12 94 |
| TOTAL LBMOL/HR | 7217.81 | 3462.92 | 3754 89 | 3462 92 | 3417 45 | 1935 67 | 1609 35 | 4050 03 | 1359 84 | 1890.19 |
| MASS FLOW LB/HR | 142766 | 44774 | 97992 | 44774 | 40727 | 52131 | 26634 | 90329 | 21995 | 48083 |
| VOLUME FLOW MMSCFD | 66 | 32 | — | — | 31 | — | 15 | — | 12 | — |
| MOLE. WT | 1978 | 12.93 | 26.10 | 12.93 | 11.92 | 26.93 | 16.55 | 22.30 | 16 10 | 25.44 |
| DENSITY LB/FT$^3$ | 2 13 | 2 82 | 28 62 | 0.71 | 0.63 | 33 86 | 1 07 | 3 84 | 1 03 | 31 33 |
| TEMPERATURE °F. | 100 | −89 | −89 | −171 | −183 | −175 | −146 | −152 | −152 | −152 |
| PRESSURE PSIA | 581 00 | 726.00 | 726.00 | 148.60 | 145.00 | 213.00 | 185.00 | 181.00 | 181 00 | 213 00 |

| STREAM NAME | STREAM NUMBER | | | | | Percent Recovered to Volatile Fraction | Percent Recovered To Less Volatile Fraction |
|---|---|---|---|---|---|---|---|
|  | 25 | 26 | 15 | 22 | 21 | | |
| HYDROGEN | 0.41 | 0.41 | 0.00 | 0 00 | 1274 20 | 100 00% | 0 00% |
| NITROGEN | 1.34 | 1 34 | 0 00 | 0 00 | 197.11 | 100 00% | 0 00% |
| CARBON MONOXIDE | 0 14 | 0 14 | 0 00 | 0 00 | 13 01 | 100 00% | 0 00% |
| METHANE | 356.91 | 356.90 | 4.21 | 4.21 | 3190 39 | 99 87% | 0 13% |
| ETHYLENE | 109 14 | 109.14 | 616.58 | 616 58 | 56 24 | 8 36% | 91 64% |
| ETHANE | 244 26 | 244 27 | 1357 22 | 1357 22 | 45 32 | 3 23% | 96.77% |
| PROPENE | 36.71 | 36.71 | 194.82 | 194 82 | 0 65 | 0 33% | 99 67% |
| PROPANE | 29 61 | 29 61 | 156 21 | 156 21 | 0 34 | 0 22% | 99.78% |
| I-BUTANE | 0 29 | 0 29 | 1 51 | 1 51 | 0 00 | 0 00% | 99 97% |
| N-BUTANE | 15 71 | 15 71 | 81 71 | 81 71 | 0 02 | 0 02% | 99 98% |
| N-PENTANE | 5 48 | 5 48 | 28 36 | 28 36 | 0 00 | 0 00% | 100 00% |
| TOTAL LBMOL/HR | 800 00 | 800 00 | 2440 62 | 2440 62 | 4777 28 | | |
| MASS FLOW LB/HR | 20351 | 20351 | 80146 | 80146 | 62622 | | |
| VOLUME FLOW MMSCFD | — | — | — | — | — | | |
| MOLE WT | 25 44 | 25 44 | 32 84 | 32 84 | | | |
| DENSITY LB/FT$^3$ | 31 33 | 31 33 | 30 51 | 23 64 | | | |
| TEMPERATURE °F. | −152 | −152 | −7 | 74 | | | |
| PRESSURE PSIA | 213.00 | 213 00 | 585 00 | 580 00 | | | |

We claim:

1. An apparatus for separating a feed gas containing at least methane, $C_2$ components and heavier components, said apparatus comprising:
   (a) a first separation means for receiving feed gas and for providing a first residue vapor and a first liquid containing $C_2$ which liquid also contains lighter hydrocarbons;
   (b) a heavy-ends fractionation column means connected to receive at least a portion of a first part of said first liquid containing $C_2$, the heavy-ends fractionation column means being adapted to separate the first liquid $C_2$ into a second residue vapor containing lighter hydrocarbons and a second liquid containing $C_2$ product;
   (c) a light-ends fractionation column means connected to said first separation means to receive at least part of said first residue vapor, said light-ends fractionation column means having at least one contacting stage, means for removing a fourth vapor, and means for removing a fourth liquid, said means for removing said fourth liquid being connected to said heavy-ends fractionation column;
   (d) a reflux separator positioned between said first separation means and said heavy ends fractionation column, means for supplying at least part of a second part of said first liquid containing $C_2$ to said reflux separator, means for removing a third liquid from said reflux separator, and means for removing a third residue vapor from said reflux separator;
   (e) means for delivering a first part of said third liquid to a heat exchanger to cool said first part of said third liquid, and means for delivering at least part of the cooled first part of said third liquid from said heat exchanger to said light-ends fractionation column means, wherein said at least part of said first residue vapor and said at least part of the cooled first part of the third liquid commingle in said at least one contacting stage, and
   (f) means for delivering a second part of said third liquid to said heavy-ends fractionation column means.

2. An apparatus according to claim 1, wherein said light-ends fractionation column comprises fractionation means for counter-current vapor-liquid contact and wherein said light-ends fractionation column is connected to receive said first residue vapor therein below said fractionation means.

3. An apparatus according to claim 2, wherein the connection for receiving said at least part of said first residue in said light-ends fractionation column is positioned below said fractionation means, and said means for delivering at least part of the cooled first part of said third liquid from said heat exchanger to said light-ends fractionation column means is connected to said light-ends fractionation column means above said fractionation means.

4. An apparatus for separating a hydrocarbon feed gas into a lighter fraction containing methane and a heavier fraction containing $C_2$ hydrocarbons, said apparatus comprising:
   a separator, said separator comprising an inlet for receiving a hydrocarbon feed gas containing methane, $C_2$ hydrocarbons, and heavier hydrocarbons, a first outlet for discharging a first residue vapor, and a second outlet for discharging a first liquid,
   a light-ends fractionation column, said light-ends fractionation column comprising a first inlet for introducing at least a part of said first residue vapor, a first outlet for discharging a fourth residue vapor containing methane, and a second outlet for discharging a fourth liquid,
   means for delivering said at least a part of said first residue vapor from said first outlet of said separator to said first inlet of said light-ends fractionation column,
   a heavy-ends fractionation column, said heavy-ends fractionation column comprising a first inlet for introducing at least a portion of said first liquid, a first outlet for discharging a second residue vapor, and a second outlet for discharging a second liquid containing $C_2$ hydrocarbons,
   means for delivering said at least a portion a first part of said first liquid from said second outlet of said separator to said first inlet of said heavy-ends fractionation column,
   a reflux separator, said reflux separator comprising an inlet for introducing at least a portion of a second part of said first liquid, a first outlet for discharging a third residue vapor, and a second outlet for discharging a third liquid, and
   means for delivering said at least a portion a second part of said first liquid from said second outlet of said separator to said inlet of said reflux separator.

5. An apparatus according to claim 4, further comprising means for delivering at least a portion of said fourth liquid from said second outlet of said light-ends fractionation column to said first inlet of said heavy-ends fractionation column.

6. An apparatus according to claim 4, further comprising means for delivering said at least a portion of said second residue vapor from said first outlet of said heavy-ends fractionation column to a second inlet of said light-ends fractionation column.

7. An apparatus according to claim 5, further comprising means for delivering said at least a portion of said second residue vapor from said first outlet of said heavy-ends fractionation column to a second inlet of said light-ends fractionation column.

8. An apparatus according to claim 4, further comprising means for delivering said at least a portion of a first part of said third liquid to a second inlet of said light-ends fractionation column.

9. An apparatus according to claim 7, further comprising means for delivering said at least a portion of a first part of said third liquid to a second inlet of said light-ends fractionation column.

10. An apparatus according to claim 4, further comprising means for delivering said at least a portion of a second part of said third liquid to a second inlet of said heavy-ends fractionation column.

11. An apparatus according to claim 9, further comprising means for delivering said at least a portion of a second part of said third liquid to a second inlet of said heavy-ends fractionation column.

12. An apparatus according to claim 4, further comprising means for delivering at least a portion of said second residue vapor from said first outlet of said heavy-ends fractionation column to said inlet of said reflux separator.

13. An apparatus according to claim 11, further comprising means for delivering at least a portion of said second residue vapor from said first outlet of said heavy-ends fractionation column to said inlet of said reflux separator.

14. An apparatus according to claim 4, further comprising means for combining said third residue vapor and said fourth residue vapor, said means for combining being connected to said first outlet of said reflux separator and connected to said first outlet of said light-ends fractionation column.

15. An apparatus according to claim 4, further comprising a turbo expartder for expartding said first residue vapor prior to being introduced into said light-ends fractionation column.

16. An apparatus according to claim 8, further comprising a heat exchanger for cooling said at least a portion of said first part of said third liquid prior to being introduced into said light-ends fractionation column.

17. An apparatus according to claim 9, further comprising a heat exchanger for cooling said at least a portion of said first part of said third liquid prior to being introduced into said light-ends fractionation column.

18. An apparatus according to claim 1, wherein said means for delivering at least part of the cooled first part of said third liquid to said light-ends fractionation column means further comprises means for combining at least a portion of said second residue vapor from said heavy-ends fractionation column with said at least part of the cooled first part of said third liquid before introduction into said light-ends fractionation column means.

19. An apparatus according to claim 1, further comprising means for combining said third residue vapor from said reflux separator with said fourth vapor from said light-ends fractionation column means.

20. An apparatus according to claim 1, further comprising means for combining said at least a portion of a first part of said first liquid containing $C_2$ and fourth liquid from said light-ends fractionation column means before being introduced into said heavy-ends fractionation column means.

\* \* \* \* \*